(12) United States Patent
Hsiao

(10) Patent No.: US 10,842,901 B2
(45) Date of Patent: Nov. 24, 2020

(54) PLUG-IN FRAGRANCE DISPENSER

(71) Applicant: DONGGUAN YIH TEH ELECTRIC PRODUCTS CO., LTD., Dongguan (CN)

(72) Inventor: Ming Jen Hsiao, Miaoli County (TW)

(73) Assignee: DONGGUAN YIH TEH ELECTRIC PRODUCTS CO., LTD., Dongguan (CN)

( * ) Notice: Subject to any disclaimer, the term of this patent is extended or adjusted under 35 U.S.C. 154(b) by 341 days.

(21) Appl. No.: 15/866,181

(22) Filed: Jan. 9, 2018

(65) Prior Publication Data

US 2018/0126025 A1 May 10, 2018

Related U.S. Application Data

(63) Continuation-in-part of application No. 15/653,362, filed on Jul. 18, 2017, and a continuation-in-part of application No. 15/258,757, filed on Sep. 7, 2016, now Pat. No. 10,064,969, and a continuation-in-part of application No. 14/938,564, filed on Nov. 11, 2015, now abandoned.

(51) Int. Cl.
*A61L 9/03* (2006.01)

(52) U.S. Cl.
CPC .............. *A61L 9/03* (2013.01); *A61L 2209/12* (2013.01); *A61L 2209/131* (2013.01); *A61L 2209/133* (2013.01)

(58) Field of Classification Search
CPC ........... A61L 9/02–037; A61L 2209/12; A61L 2209/131; A61L 2209/133; A01M 1/2061; A01M 1/2077
See application file for complete search history.

(56) References Cited

U.S. PATENT DOCUMENTS

| 6,638,588 | B1 * | 10/2003 | Bowen | A01M 1/2061 |
| | | | | 206/484 |
| 8,192,041 | B2 | 6/2012 | Hsiao | |
| 8,201,957 | B2 | 6/2012 | Hsiao | |
| 8,262,277 | B2 * | 9/2012 | Hsiao | A61L 9/03 |
| | | | | 362/643 |

(Continued)

FOREIGN PATENT DOCUMENTS

| EP | 2679249 A1 | 1/2014 |
| GB | 2505450 A | 3/2014 |

*Primary Examiner* — Tu B Hoang
*Assistant Examiner* — Erin E McGrath
(74) *Attorney, Agent, or Firm* — Sinorica, LLC

(57) ABSTRACT

A plug-in fragrance dispenser contains: a body, an electric plug, a heating element, a heat transfer plate, and a holder. The electric plug is electrically connected with a power source, and the body is coupled with the electric plug and includes a first orifice, a first connection part, and a second connection part. The first connection part is connected with the second connection part, the first connection part has an accommodation lid and a surround sleeve, and the surround sleeve has the first orifice defined on a top thereof. The accommodation lid has a second orifice in which the electric plug is accommodated, the second connection part has a support seat and a first cap formed on an upper end of the support seat and connecting with a bottom of the surround sleeve, wherein the support seat is housed in the accommodation lid.

10 Claims, 4 Drawing Sheets

(56) References Cited

U.S. PATENT DOCUMENTS

| | | |
|---|---|---|
| 8,668,885 B2 | 3/2014 | Wirz |
| 8,765,073 B1 | 7/2014 | Shbvi |
| 8,787,739 B2 | 7/2014 | Hsiao |
| 8,983,277 B2 | 3/2015 | Hsiao |
| 9,028,759 B2 | 5/2015 | Hsiao |
| 9,031,392 B2 | 5/2015 | Hsiao |
| 9,206,963 B2 | 12/2015 | Hsiao |
| 9,410,695 B2 | 8/2016 | Hsiao |
| 9,498,553 B2 | 11/2016 | Shbvi |
| 2011/0110824 A1 | 5/2011 | Hsiao |
| 2014/0110389 A1 | 4/2014 | Hsiao |
| 2015/0109823 A1* | 4/2015 | Hsiao ............ A61L 9/03 362/643 |
| 2015/0117056 A1 | 4/2015 | Hsiao |
| 2015/0374871 A1* | 12/2015 | Chew ............ A01M 1/2044 239/6 |
| 2016/0195257 A1 | 7/2016 | Hsiao |

* cited by examiner

PLUG-IN FRAGRANCE DISPENSER

CROSS-REFERENCES TO RELATED APPLICATION

The present invention is a continuation-in-part of patent application Ser. No. 14/938,564 filed on Nov. 11, 2015 and Ser. No. 15/258,757 filed on Sep. 7, 2016 and patent application Ser. No. 15/653,362 filed on Jul. 18, 2017.

BACKGROUND OF THE INVENTION

Field of the Invention

The present invention relates to a plug-in fragrance dispenser.

Description of the Prior Art

A conventional fragrance heating dispenser is disclosed in U.S. Pat. Nos. 8,066,420, 8,262,277, and US Pub. No. 2012/0024837A1, the fragrance heating dispenser contains a power source and a heating source, but it is dangerous to cause fire when essential oil or wax leaks out of the fragrance heating dispenser. Furthermore, it is troublesome to wash the fragrance heating dispenser after removing the essential oil or wax. Aroma-diffusing heating device is disclosed in U.S. Pat. Nos. 8,668,885, 9,550,358, 9,498,553 and EP Pat. No. 2679249, the aroma-diffusing heating device contains a breathing film made of plastic, but such a breathing film deforms and wrinkles easily after a period of using time.

Conventional plug-in fragrance illumination dispenser contains LED chips which emit lights within 120 degrees only, thus limiting illumination range.

The present invention has arisen to mitigate and/or obviate the afore-described disadvantages.

SUMMARY OF THE INVENTION

The primary aspect of the present invention is to provide a plug-in fragrance dispenser in which a disposable aroma capsule is accommodated.

Another aspect of the present invention is to provide a plug-in fragrance dispenser which emits lights 360 degrees.

To obtain the above aspects, a plug-in fragrance dispenser provided by the present invention contains: a body, an electric plug, a heating element, a heat transfer plate, and a holder.

The electric plug is configured to electrically connect with a power source. The body is coupled with the electric plug and includes a first orifice defined on a top of the body.

The heating element is accommodated in the body and is electrically connected with the electric plug, and the heat transfer plate is housed in the body and contacts with the heating element.

The body further includes a first connection part and a second connection part, the first connection part is in connection with the second connection part so as to form the body, the first connection part has an accommodation lid and a surround sleeve arranged on an upper end of the accommodation lid, and the surround sleeve has the first orifice defined on a top thereof, the accommodation lid has a second orifice in which the electric plug is accommodated. The second connection part has a support seat and a first cap formed on an upper end of the support seat and connecting with a bottom of the surround sleeve, wherein the support seat is housed in the accommodation lid.

In addition, holder is connected on a bottom of the first cap.

DETAILED DESCRIPTION OF THE PREFERRED EMBODIMENTS

Figure 1:
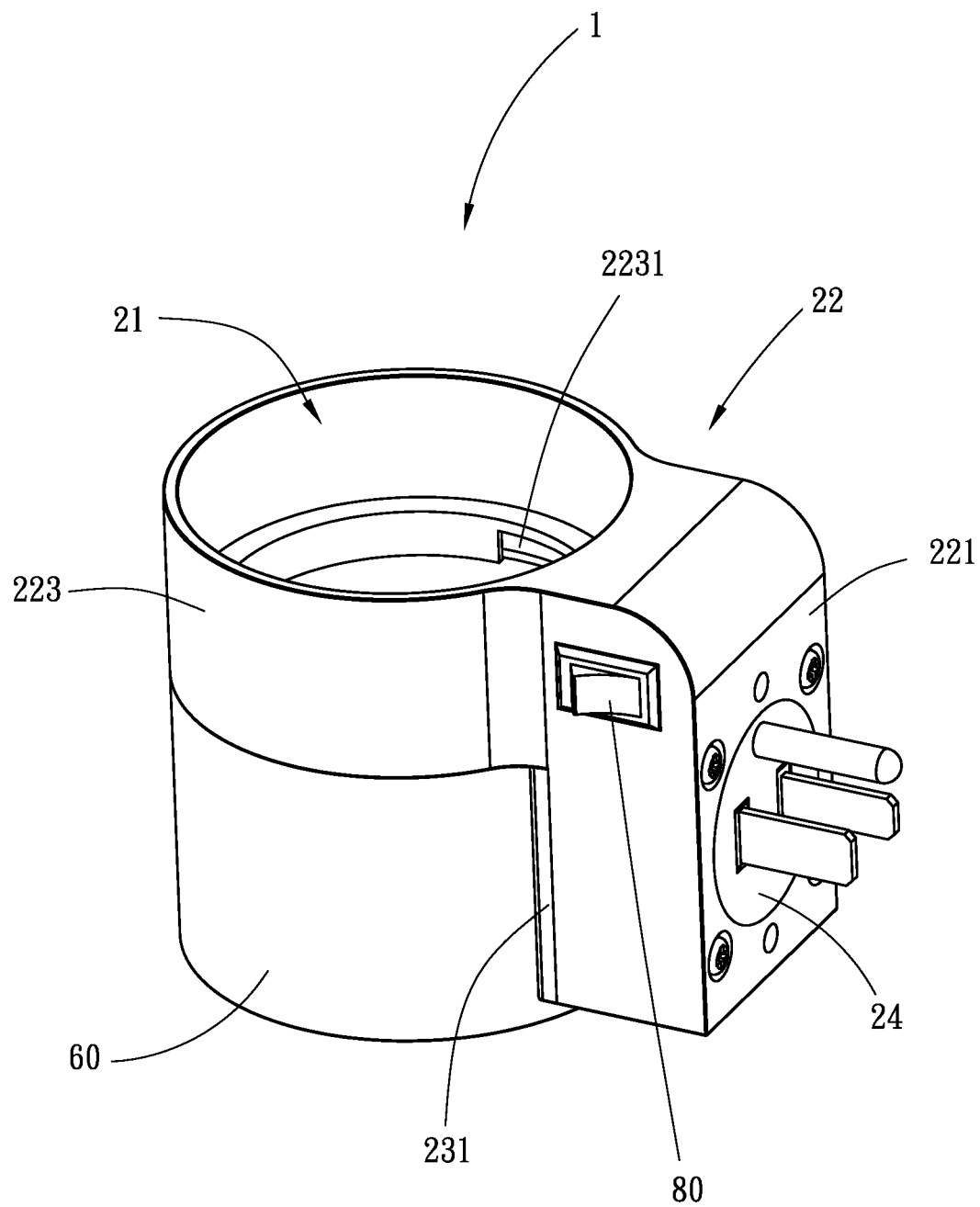
FIG. 1 is a perspective view showing the assembly of a plug-in fragrance dispenser according to a preferred embodiment of the present invention.
Figure 2:
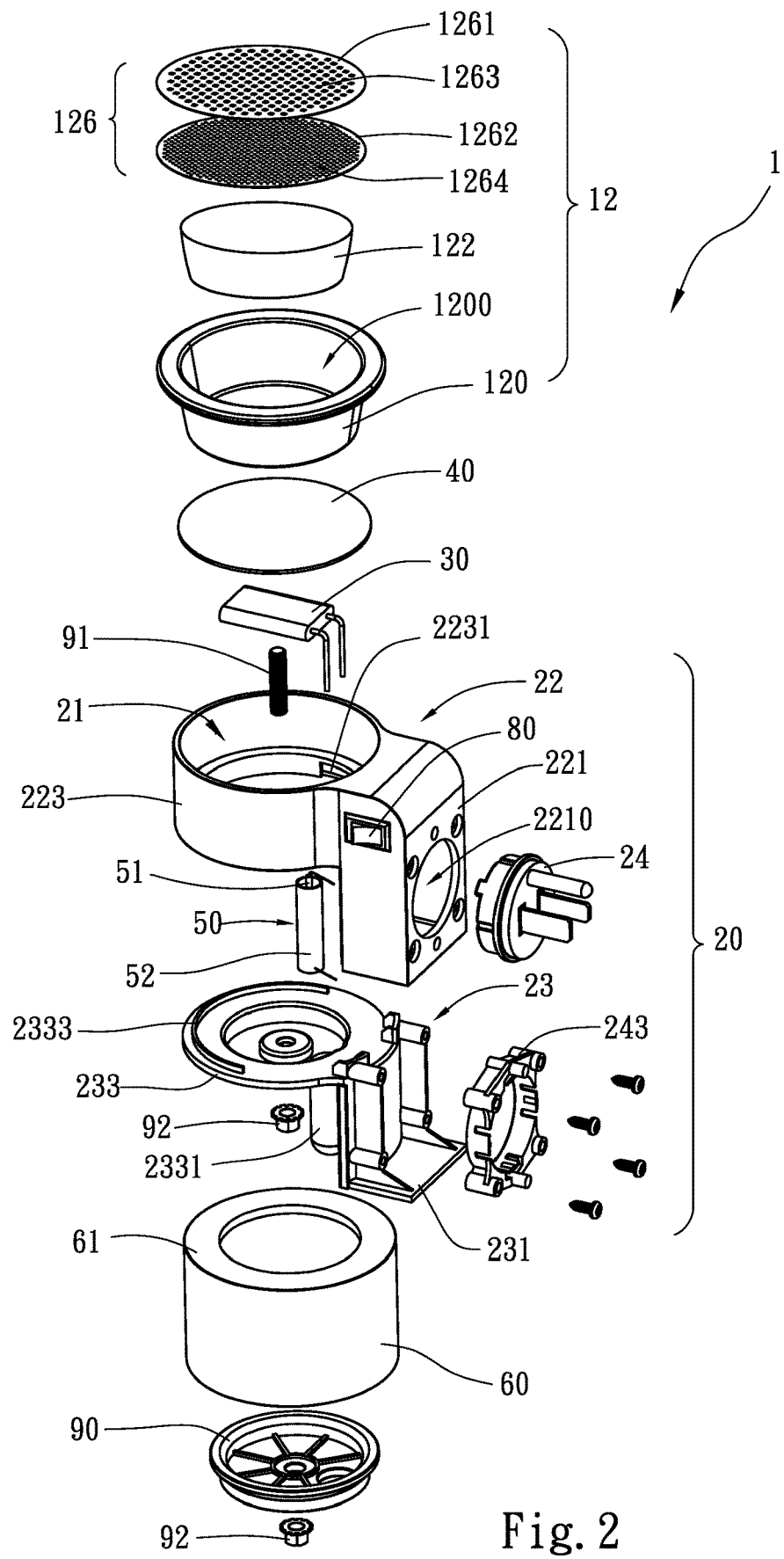
FIG. 2 is a perspective view showing the exploded components of the plug-in fragrance dispenser and an aroma capsule according to the preferred embodiment of the present invention.
Figure 3:
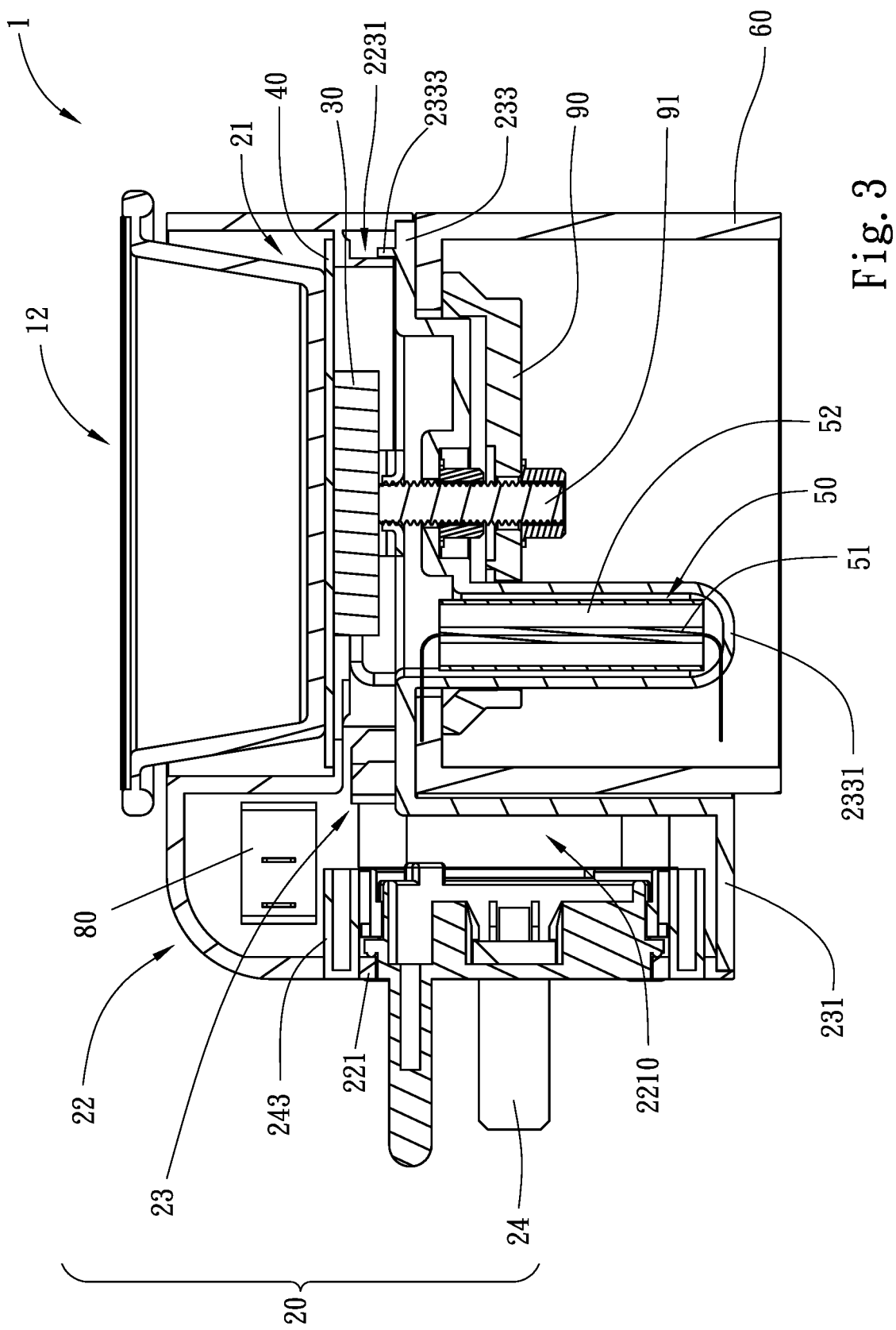
FIG. 3 is a cross sectional view showing the assembly of the plug-in fragrance dispenser and the aroma capsule according to the preferred embodiment of the present invention.

With reference to FIGS. 1-3, a plug-in fragrance dispenser 1 according to a preferred embodiment of the present invention comprises: a body 20 and an electric plug 24 configured to electrically connect with a power source.

The body 20 is coupled with the electric plug 24, and the body 20 includes a first orifice 21 defined on a top thereof. The plug-in fragrance dispenser 1 further comprises a heating element 30 accommodated in the body 20 and electrically connected with the electric plug 24, and a heat transfer plate 40 housed in the body 20 and contacting with the heating element 30.

The body 20 further includes a first connection part 22 and a second connection part 23. The first connection part 22 is in connection with the second connection part 23 so as to form the body 20. The first connection part 22 has an accommodation lid 221 and a surround sleeve 223 arranged on an upper end of the accommodation lid 221, and the surround sleeve 223 has the first orifice 21 defined on a top thereof. The accommodation lid 221 has a second orifice 2210 in which the electric plug 24 is accommodated. The second connection part 23 has a support seat 231 and a first cap 233 formed on an upper end of the support seat 231 and connecting with a bottom of the surround sleeve 223, wherein the support seat 231 is housed in the accommodation lid 221.

The plug-in fragrance dispenser 1 further comprises a holder 60 connected on a bottom of the first cap 233.

The surround sleeve 223 has a locking groove 2231 formed on a lower end of an inner wall thereof, and the first cap 233 has an engagement rib 2333 arranged on a top thereof so as to retain with the locking groove 2231 of the surround sleeve 223.

The plug-in fragrance dispenser 1 further comprises an illumination device 50. The holder 60 is made of transparent material or translucent material, wherein the transparent material is any one of transparent ceramic, transparent plastic, transparent glass, ceramic with a hole, metal with a hole, and wood with a hole.

The illumination device 50 is accommodated in the holder 60 made of the transparent material, and the illumination device 50 is electrically connected with the electric plug 24, wherein the illumination device 50 includes two LED chips 51 mounted on two ends thereof respectively. In this embodiment, the holder 60 is made of transparent ceramic so that the plug-in fragrance dispenser 1 emits lights from the illumination device 50 via the holder 60.

The first cap 233 has a light guide element 2331 extending into the holder 60 from one side of the first cap 233. The illumination device 50 is fixed inside the light guide element 2331, and the light guide element 2331 is made of transparent material or translucent material, wherein the translucent material is any one of plastic, glass, acrylic, and silicone. In this embodiment, the light guide element 2331 is made of polypropylene (PP) so as to guide lights from the illumination device 50 to the holder 60.

The illumination device 50 emits the lights outwardly 360 degrees by using the two LED chips 51, thus enhancing a light emitting angle.

The plug-in fragrance dispenser 1 further comprises an aroma capsule 12 accommodated in the body 20 and contacting with the heat transfer plate 40, such that the heating element 30 heats the heat transfer plate 40 so that the aroma capsule 12 is heated to release a pleasant smell via the heat transfer plate 40. The heat transfer plate 40 is selected from the group of metal materials and their alloys. Preferably, the aroma capsule 12 is disposable or is recyclable. In this embodiment, the holder 60 is made of the transparent ceramic so that the plug-in fragrance dispenser 1 emits the lights from the illumination device 50 or/and the light guide element 2331 via the holder 60.

Figure 4:
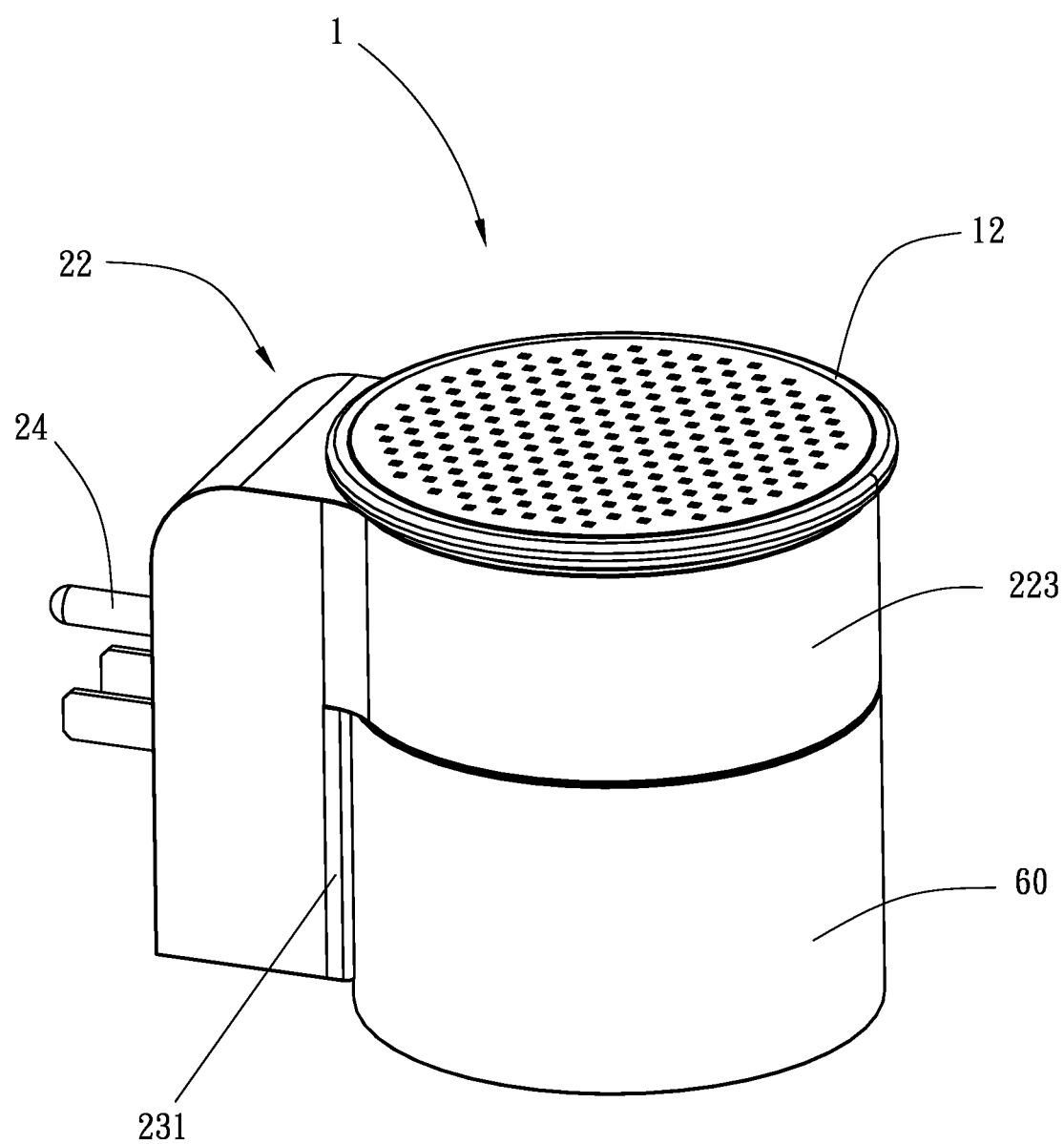
FIG. 4 is a perspective view showing the assembly of the plug-in fragrance dispenser and the aroma capsule according to the preferred embodiment of the present invention.

Referring further to FIGS. 1, 2, and 4, the electric plug 24 is inserted into a wall socket at different angles, and the electric plug 24 has a base 243 and a rotatable plug 241, wherein the base 243 is housed in the second orifice 2210 of the accommodation lid 221, and the rotatable plug 241 is rotatably connected on the base 243, hence the rotatable plug 241 is adjustably rotated relative to the base 243 and the body 20 based on using requirements. For example, the aroma capsule 12 is heated and is parallel to the wall socket. In this embodiment, the rotatable plug 241 is rotated 270 degrees and is fixed as being rotated to a desired angle (such as 90 degrees).

The heating element 30 is any one of a cement resistor, a thermistor, and positive thermal coefficient (PCT) thermistor.

As shown in FIGS. 2 and 3, the illumination device 50 includes a transparent polycarbonate (PC) tube 52 configured to protect the illumination device 50. The illumination device 50 is in an elongated strap shape, and the illumination device 50 includes multiple LED chips arranged on the two sides thereof (such as on each 180-degree position of the illumination device 50) respectively or on each 90-degree position of the illumination device 50 individually, thus emitting the lights 360 degrees from the illumination device 50.

In another embodiment, the holder 60 includes a first opening defined on a top thereof, a second opening formed on a bottom of the holder 60, a protruded extension 61 arranged around the first opening of the holder 60.

The plug-in fragrance dispenser 1 further comprises a fixing disc 90 in which a connection post 91 is inserted, and the connection post 91 (such as a thread rod) is screwed with multiple screwing elements 92 and the fixing disc 90 via the holder 60 and the body 20, wherein the multiple screwing elements 92 connect with the fixing disc 90, and the fixing disc 90 forces the protruded extension 61 to matingly contact with the body 20, thus connecting the holder 60 with the body 20.

Referring to FIGS. 2-4, the aroma capsule 12 comprises a heat-transfer container 120 defining a top opening 1200, an aromatic substance 122 held in the heat-transfer container 120, and a breathing film bonded to the heat-transfer container 120 over the top opening 1200 and the aromatic substance 122 so as to allow moisture vapor to be transmitted through the material.

Referring to FIGS. 2-4, the breathing film 126 comprises a fiber fixation layer 1261 and a microporous layer 1262 of excellent moisture permeability. The fiber fixation layer 1261 defines therein multiple first pores 1263. The microporous layer 1262 defines therein multiple second pores 1264. The fiber fixation layer 1261 and the microporous layer 1262 are bonded together to form the breathing film 126 with the breathable and waterproof function. The microporous layer 1262 is preferably made out of thermoplastic elastomer (TPE) compound. The fiber fixation layer 1261 is preferably made out of thermoplastic elastomer (TPE) compound or polyester. The polyester fiber fixation layer 1261 and the thermoplastic elastomer (TPE) microporous layer 1262 are bonded together to form the breathing film 126 that is breathable. The breathable aperture of the first pores 1263 is greater than the breathable aperture of the second pores 1264, facilitating outward transmittance of air. The breathing film 126 is bonded to the heat-transfer container 120 over the top opening 1200. Through the second pores 1264 of the thermoplastic elastomer (TPE) microporous layer 1262, the aroma capsule 12 provides waterproof and moisture transmissive functions, keeping the aromatic substance 122 fresh.

The thermoplastic elastomer (TPE) microporous layer 1262 and the fiber fixation layer 1261 can be bonded together using hot-press fusion or high-frequency sealing technology. Since the first pores 1263 of the fiber fixation layer 1261 are relatively lager than the second pores 1264 of the thermoplastic elastomer (TPE) microporous layer 1262, the heated aromatic substance vapor molecules can go through second pores 1264 of the thermoplastic elastomer (TPE) microporous layer 1262 toward the first pores 1263 of the fiber fixation layer 1261.

In application, the aroma capsule 12 is heated in the plug-in fragrance dispenser 1 to release the pleasant smell at a temperature below 90° C. During the heating process, the fiber fixation layer 1261 does not shrink or expand the size and can keep the thermoplastic elastomer (TPE) microporous layer 1262 in shape, and thus, the surface of the breathing film 126 can be constantly maintained smooth without wrinkles. During the heating process, aromatic substance 122 keeps releasing aromatic vapor molecules that flow smoothly through the second pores 1264 of the thermoplastic elastomer (TPE) microporous layer 1262 and the first pores 1263 of the fiber fixation layer 1261 toward the atmosphere outside the aroma capsule 12, however, the liquid phase aromatic substance is prohibited from passing through the second pores 1264, ensuring safety application of the aroma capsule 12.

Further, the aromatic substance 122 is selected from the group consisting of aromatic wax, perfume, balsam, sesame oil mixture and essential oil. In the case an aromatic wax is used for the aromatic substance 122 of the aroma capsule 12, the plug-in fragrance dispenser 1 simply needs to heat the aromatic wax to the melting point of the aromatic wax, causing the aromatic wax to release aromatic vapor molecules through the breathing film 126 toward the outside open air. In the case a sesame oil mixture or essential oil is used for the aromatic substance 122 of the aroma capsule 12, the sesame oil mixture or essential oil is heated to release aromatic vapor molecules through the breathing film 126 toward the outside open air. When compared to related existing commercial products, the breathing film 126 of the present invention will not deform during the heating process, and the released aromatic vapor molecules can flow through the breathing film 126 toward the outside open air efficiently.

Further, the heat-transfer container 120 is made out of polymers. In one embodiment, the heat-transfer container 120 is made out of plastics selected from the group consisting of polyester plastic, poly chloro terephthalate glycol (PCTG), polyethylene terephthalate (PET), propylthiouracil (PTU) and polypropylene (PP). The plastic heat-transfer container 120 does not melt or deform at the above-mentioned heating temperature, and can efficiently transfer heat energy from the plug-in fragrance dispenser 1 to the aromatic substance 122. In one embodiment of the present invention, the heat-transfer container 120 is made out of PCTG, capable of transferring heat energy from the plug-in fragrance dispenser 1 to the aromatic substance 122 for causing the aromatic substance 122 to release a pleasant smell. Further, the heat-transfer container 120 has excellent ductility and toughness and is not easy to rapture. It will not be damaged when heating by the aroma-diffusing heating device, and can efficiently transfer heat energy from the aroma-diffusing heating device to the aromatic substance. When compared to fragile pottery and glass heat-transfer containers of conventional aroma-diffusing heating devices, the heat-transfer container 120 has the advantage that the top opening 1200 of the heat-transfer container 120 can easily be bonded with the breathing film 126, i.e., the thermoplastic microporous layer 1262 of the breathing film 126 can be bonded to the top opening 1200 of the heat-transfer container 120 by heat or with an adhesive. The bonding effect is better than the prior art design. After bonding, the breathing film 126 will not fall off.

In another embodiment, the plug-in fragrance dispenser 1 further comprises a switch device 80 electrically connected with the electric plug 24, the heating element 30, and the illumination device 50 so as to turn on/off the heating element 30 and the illumination device 50.

While the preferred embodiments of the invention have been set forth for the purpose of disclosure, modifications of the disclosed embodiments of the invention as well as other embodiments thereof may occur to those skilled in the art. The scope of the claims should not be limited by the preferred embodiments set forth in the examples, but should be given the broadest interpretation consistent with the description as a whole.

What is claimed is:

1. A plug-in fragrance dispenser comprising:
   a body and an electric plug configured to electrically connect with a power source; the body being coupled with the electric plug, and the body including a first orifice defined on a top of the body; a heating element accommodated in the body and electrically connected with the electric plug; a heat transfer plate housed in the body and contacting with the heating element; and an illumination device;
   wherein the body further includes a first connection part and a second connection part, the first connection part is in connection with the second connection part so as to form the body, the first connection part has an accommodation lid and a surround sleeve arranged on an upper end of the accommodation lid, and the surround sleeve has the first orifice defined on a top thereof, the accommodation lid has a second orifice in which the electric plug is accommodated; the second connection part has a support seat and a first cap formed on an upper end of the support seat and connecting with a bottom of the surround sleeve, wherein the support seat is housed in the accommodation lid;
   wherein a holder is connected on a bottom of the first cap, wherein the holder is made of transparent material or translucent material, the illumination device is accommodated in the holder, and the illumination device is electrically connected with the electric plug, wherein the illumination device includes two light emitting diode (LED) chips mounted on two ends thereof respectively.

2. The plug-in fragrance dispenser as claimed in claim 1, wherein the surround sleeve has a locking groove formed on a lower end of an inner wall thereof, and the first cap has an engagement rib arranged on a top thereof so as to retain with the locking groove of the surround sleeve.

3. The plug-in fragrance dispenser as claimed in claim 1, wherein the first cap has a light guide element extending into the holder from one side of the first cap, and the illumination device is fixed inside the light guide element, wherein the light guide element is made of transparent material or translucent material.

4. The plug-in fragrance dispenser as claimed in claim 1, wherein the electric plug is inserted into a wall socket at different angles, and the electric plug has a base and a rotatable plug, wherein the base is housed in the second orifice of the accommodation lid, and the rotatable plug is rotatably connected on the base.

5. The plug-in fragrance dispenser as claimed in claim 1, wherein the heating element is any one of a cement resistor, a thermistor, and positive thermal coefficient (PTC) thermistor.

6. The plug-in fragrance dispenser as claimed in claim 1, wherein the illumination device includes a transparent polycarbonate (PC) tube configured to protect the illumination device, and the illumination device is in an elongated strap shape.

7. The plug-in fragrance dispenser as claimed in claim 3, wherein the illumination device includes a transparent polycarbonate (PC) tube configured to protect the illumination device, and the illumination device is in an elongated strap shape.

8. The plug-in fragrance dispenser as claimed in claim 1 further comprising a fixing disc in which a connection post is inserted, wherein the connection post is a thread rod screwed with multiple screwing elements and the fixing disc via the holder and the body, the multiple screwing elements connect with the fixing disc, and the fixing disc forces a protruded extension of the holder to matingly contact with the body, thus connecting the holder with the body.

9. The plug-in fragrance dispenser as claimed in claim 1 further comprising an aroma capsule accommodated in the body, wherein the aroma capsule includes a heat-transfer container defining a top opening, an aromatic substance held in the heat-transfer container, and a breathing film bonded to the heat-transfer container over the top opening and the aromatic substance, the breathing film includes a fiber fixation layer and a microporous layer, the fiber fixation layer defines therein multiple first pores, the microporous layer defines therein multiple second pores, wherein the fiber fixation layer and the microporous layer are bonded together to form the breathing film.

10. The plug-in fragrance dispenser as claimed in claim 9, wherein the microporous layer is made out of thermoplastic elastomer (TPE) compound, and the fiber fixation layer is made out of thermoplastic elastomer (TPE) compound or polyester.

* * * * *